United States Patent
Mordukhovich et al.

(10) Patent No.: US 11,160,854 B2
(45) Date of Patent: Nov. 2, 2021

(54) IMMUNOSTIMULATORY PREPARATION EXHIBITING ANTITUMOR ACTIVITY

(71) Applicant: LIMITED LIABILITY COMPANY "CANCERNET", Moscow (RU)

(72) Inventors: Eduard Isaakovich Mordukhovich, Moscow (RU); David Borisovich Zhukov, Moscow (RU); Ilya Vladimirovich Darmov, Kirov (RU); Veronika Yuryevna Okhapkina, Kirov (RU)

(73) Assignee: Limited Liability Company "Cancernet", Moscow (RU)

( * ) Notice: Subject to any disclaimer, the term of this patent is extended or adjusted under 35 U.S.C. 154(b) by 0 days.

(21) Appl. No.: 16/300,556

(22) PCT Filed: Jul. 11, 2016

(86) PCT No.: PCT/RU2016/000427
§ 371 (c)(1),
(2) Date: Nov. 10, 2018

(87) PCT Pub. No.: WO2018/012994
PCT Pub. Date: Jan. 18, 2018

(65) Prior Publication Data
US 2020/0030429 A1    Jan. 30, 2020

(51) Int. Cl.
*A61K 39/02* (2006.01)
*A61P 37/04* (2006.01)
*A61P 35/00* (2006.01)
*A61K 9/00* (2006.01)
*C12N 1/20* (2006.01)
*A61K 39/00* (2006.01)

(52) U.S. Cl.
CPC ........ *A61K 39/0225* (2013.01); *A61K 9/0029* (2013.01); *A61K 39/098* (2013.01); *A61P 35/00* (2018.01); *A61P 37/04* (2018.01); *C12N 1/20* (2013.01); *A61K 2039/521* (2013.01); *A61K 2039/54* (2013.01); *A61K 2039/585* (2013.01); *A61K 2039/70* (2013.01)

(58) Field of Classification Search
None
See application file for complete search history.

(56) References Cited

U.S. PATENT DOCUMENTS

2011/0229503 A1    9/2011   Krone et al.

FOREIGN PATENT DOCUMENTS

| EP | 2109452 | 8/2008 |
|---|---|---|
| RU | 2141339 | 11/1999 |
| RU | 2216743 | 11/2003 |
| WO | WO2012158978 | 11/2012 |

OTHER PUBLICATIONS

Rivista dell'Istituto Sieroterapico Italiano (1957), 32, 489-500. Note: Abstract Only.*
Christiansen A.H. et al. The Reiter strain of Treponema pallidum. Armis 1963, vol. 57, No. 1, pp. 81-86.
Frederick L. et al. The cultivation of anaerobic treponemata on the surface of blood agar plates. The journal of experimental medicine 1992, vol. XXXVII, p. 311-317.
Spirolate Broth, OMATA—HiMedia Labs. Revision: Jan. 2011. http://himedialabs.com/TD/M412.pdf, p. 1-2.

* cited by examiner

*Primary Examiner* — Jennifer E Graser
(74) *Attorney, Agent, or Firm* — Aleksandr Smushkovich

(57) ABSTRACT

The proposed preparation and methods relate to medicinal microbiology and pharmacology, and relate to preparations exhibiting an immunostimulatory effect, which may be used for the prevention and treatment of oncological diseases. The essence of the preparation and methods consists in a primary component of the preparation including a polyvalent corpuscular antigen, prepared on the basis of *Treponema pallidum* culture strains. The proposed preparation exhibits an immunostimulatory effect, with a primary influence on components of T-cell immunity. The proposed preparation, in a preventative therapeutic application, is effective with regard to tumors of various histogenesis.

10 Claims, 1 Drawing Sheet

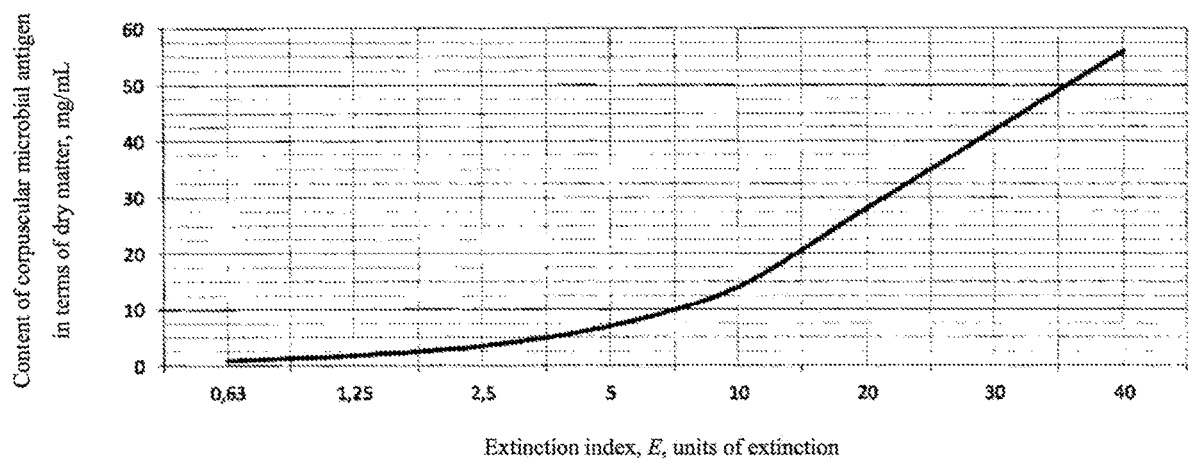

IMMUNOSTIMULATORY PREPARATION EXHIBITING ANTITUMOR ACTIVITY

CROSS-REFERENCE TO RELATED APPLICATIONS

This application is a U.S. national stage application of a PCT application PCT/RU2016/000427 filed on 11 Jul. 2016, published as WO/2018/012994, whose disclosure is incorporated herein in its entirety by reference.

FIELD OF INVENTION

The present invention relates to the field of medical microbiology and pharmacology and can be used for the prevention and therapy of malignant neoplasms. Further, the invention relates to a method of preventing and treating oncological diseases, specifically a novel antigenic preparation produced on the basis of *Treponema pallidum* culture strains, as well as methods for its preparation and use.

To date, a large amount of data has been collected confirming the effectiveness of the use of preparations based on microbial-origin immunostimulants in case of tumor diseases with various localization and at different stages of the process. Although such agents exhibit no direct antitumor and antimetastatic effects, they have the ability to enhance antitumor immunity by enhancing and/or restoring the effector mechanism mediated through the presentation function of macrophages, the regulation of the synthesis of interleukin-1 (IL-1), tumor necrosis factor (TNF), interleukin-2 (IL-2), natural killers (NK cells), etc., and can also modify other biological aspects of the host-tumor relationship.

BACKGROUND OF THE INVENTION

Two preparations obtained on the basis of a protozoan (*Trypanosoma cruzi*), namely, Crucinum™ in Russia (USSR) and *Trypanosoma*™ in France (Klyueva N. G. Biotherapy of malignant tumors//Bulletin of the Academy of Medical Sciences of the USSR—1946.—No. 2-3.—P. 44-53 [Rus]; Klyuyeva N. G., Roskin G. I. Biotherapy of malignant tumors. Oxford etc., 1963; Kalinnikova V. D. Antitumor properties of the flagellate protozoan *Trypanosoma cruzi*.—Tula City: Grif & Co, 2004.—280 p. [Rus]) are the earliest examples of the use of microbial factors for the therapy of human tumors. However, despite numerous reports of positive results, they have not gained wide recognition.

The use of the anti-TB vaccine BCG in clinical oncology to treat bladder cancer is known. However, the mechanism of the antitumor effect of this vaccine is not fully understood. The high reactogenicity and sensitizing properties of the vaccine when repeated administration are its disadvantages (Immunology and Allergology/ed. A. A. Vorobyova, A. S. Bykov, A. V. Karaulova. Moscow: Practical Medicine, 2006.—287 p. [Rus]).

The use of a vaccine based on the cytoplasmic membranes of the L-forms of bacteria, in particular, the causative agent of brucellosis, was proposed for cancer biotherapy. In this case, the low-grade structurally-microbial cells in the final L3-form of transformation are considered as "relic" ones, having a high degree of similarity to the cells of malignant tumors, which determines the possibility of preparing a vaccine antitumor preparation on their basis (Kazpatent No. 13,980, RU 2,409,376, Aug. 13, 2002). However, the data presented on the positive results of treatment and prevention concern benign diseases only, with no convincing information on the use of this vaccine in patients with malignant neoplasms.

The use of a living tularemia vaccine in the complex therapy of patients with cancer of the uterus body and lungs is known (RU 2,092,186 C1 Oct. 10, 1997). The disadvantage of this method is that the introduction of a living culture of a pathogenic microorganism under conditions of regular immunity disorders in cancer patients, while using cytostatic preparations, contributes to the implementation of vaccine-inherent complications and side effects associated with the accumulation and reproduction of tularemia microbes in the body: sensitization, high reactogenicity, the development of an infectious process. These complications in some cases require antibacterial therapy. In addition, considering the pathogenesis of tularemia, specific humoral links of the immune system are preferably subjected to immunostimulation, whose role in antitumor immunity is only auxiliary (secondary).

The most closely related to the present invention is the immunity-stimulating preparation (vaccine), which is a culture of a strain of bacteria *Corynebacterium krestovnicova-troitskaya*. This vaccine does not have a specific therapeutic effect on the growth of tumors, but affects them indirectly, through stimulation of the immune system (both humoral and cellular) by restoring the natural resistance to the tumor process (RU 2,027,755 C1 Jan. 27, 1995). The culture of the strain accumulates on a dense nutrient medium, is suspended, and the resulting suspension is used for administration to cancer patients. The disadvantage of this therapeutic method is that a culture of living bacteria isolated from humans is used; there is not a sufficient amount of convincing data on this strain's safety. Besides, the vaccine preparation scheme presented in the disclosure is non-technological, non-reproducible and does not allow obtaining a standard (by properties) product.

OBJECT AND BRIEF SUMMARY OF THE INVENTION

The present invention proposes the use of culture treponemes *pallidum* as a basis for the development of a tumor prevention and therapy preparation.

The causative agent of syphilis (*Treponema pallidum*) was isolated in 1905 (Schaudin et Hoffman), belongs to the species *Treponema pallidum*. During the long period of its study by infecting susceptible laboratory animals (primates, rabbits), several strains of tissue human pathogenic treponemes *pallidum* (Nicholls, Budapest, Irkutsk, VIII and XII CKVI and others) were obtained and subsequent preservation of the strains was carried out by regular transplantations to laboratory animals. Numerous attempts to grow *Treponema pallidum* on nutrient media under anaerobic conditions led to the production of such strains of culture treponemes *pallidum* as the Stavropol, Kazan, Reiter, Truffy, Mulzer (Munich) ones, etc.

The greatest number of treponemes *pallidum* culture strains in the USSR was cultured by V. M. Aristovsky and P. P. Geltzer [Ovchinnikov N. M. Experimental syphilis. —Moscow: Medgiz, 1955.—387 p, Rus]. The Kazan (V) and Stavropol (VII, VIII, and IX) strains, along with the Reiter one, are currently used to prepare antigens for serum diagnostics. It has been established that culture treponemes differs from tissue ones by their morphological, biochemical and pathogenic properties.

However, it is especially significant that their antigenic properties are very close to those of pathogenic variants of the causative agent of syphilis. What's more, none of the culture treponemes strains has pathogenicity for humans. In addition, they can be grown in required quantities under laboratory conditions, on artificial nutrient media, and stored for a long period of time through regular transplantations.

Prior art publications generally describe the use of antigenic preparations prepared from cultural treponemes for syphilis serum diagnostics. In particular, the prior art discloses a method for preparing an ultrasound-treated antigen from culture strains of treponemes, on whose basis a diagnosticum is prepared to cause a complement binding reaction. Treponemal biomass is grown on an artificial thioglycolic medium from a complete set of strains of three antigenic groups, followed by ultrasound disintegration of the cells, centrifugation, separation of intact treponemes, centrifugation of the supernatant, and isolation of the treponemes wall precipitate and the supernatant (Patent RU 2,141,339. Method for obtaining antigens from culture treponemes *pallidum*. V. O. Pozharskaya. Publ. Nov. 20, 1999, Bull. 32).

The use of cell wall antigens (treponemal cell walls, TCW) of culture treponemes *pallidum* as an immunogen is also known to produce control serum for syphilis diagnosis in a complement binding reaction (Patent RU 2,185,856. Method for obtaining control sera for syphilis diagnosis. V. O. Pozharskaya, E. A. Gurtova, A. V. Yermolov. Publ. Jul. 27, 2002, Bull. 21). The method is implemented by means of intratesticular infestation of 3.0-3.5 kg rabbits with the pathogenic Nichols strain; 7-8 days after infection the animals are twice immunized with an interval of 7-8 days, by intravenously administering cellular structures of culture treponemes *pallidum* (TCW-antigen) from culture treponemes *pallidum* with subsequent bleeding of the animals 30 days after infection. The method allows increasing the average titers of anticardiolipin antibodies in the complement binding reaction from 1:15 to 1:40 dilution in the blood of bloodless animals.

Thus, no information sources have been found from the state of the art where the use of culture treponemes *pallidum* as a basis for the development of preparations for the prevention and therapy of oncological diseases would be reported.

The object of the invention is developing an effective and safe immunity-stimulating preparation based on culture treponemes *pallidum* for the prevention and therapy of malignant neoplasms.

The achieved result is the widening of the spectrum of immunity-stimulating agents and antitumor activity along with immunity-stimulatory action.

The claimed preparation is characterized by biotechnological feasibility, efficiency and standard properties (to prepare finished products corresponding to the required quality indicators). Biotechnological feasibility is an important requirement that is specified to strains suitable for the design of vaccine preparations, to make it possible to obtain sufficient volumes of microbial mass and its long-term maintenance in a stable state under laboratory conditions.

The stated problem is solved by the fact that the immunity-stimulating preparation for the prevention or treatment of oncological diseases contains the causative agent of syphilis-*Treponema pallidum* as a basis. In various embodiments of the invention, native or inactivated corpuscular antigens prepared from *Treponema pallidum* culture strains may be used as a basis.

The best result is achieved when using a mixture of the inactivated corpuscular antigens of, at least, three laboratory treponemes strains, while strains can be taken in equal proportions, which is not mandatory. The best option is when the strains used are related to at least three antigenic groups of the pathogen. In this case, the result will be achieved even with an embodiment of the invention with one or two strains, including those taken from one antigenic group. It is possible to use the preparation where inactivated corpuscular antigens of treponemes strains sorbed on aluminum hydroxide are used as a basis.

BRIEF DESCRIPTION OF DRAWING OF THE INVENTION

FIG. 1 illustrates a calibration plot for detection of the content of corpuscular microbial antigen for various experimental samples of the proposed vaccine.

PREFERRED EMBODIMENTS OF THE INVENTION

The preparation intended for treatment of oncological diseases may contain a mixture of heat-inactivated and phenol-preserved microbes of *Treponema pallidum* culture strains (for example, 1 ml of the preparation contains 0.5±0.1 mg of a microbial antigen in terms of dry matter and 2.5±0.2 mg of phenol). The preparation intended for the prevention of oncological diseases or for antitumor immunity stimulation may contain a mixture of heat-inactivated, adsorbed on aluminum hydroxide and phenol-conserved microbes of *Treponema pallidum* culture strains (for example, 1 ml of the preparation contains 28.0±1.0 mg of corpuscular microbial antigen in terms of dry matter, 2.5±0.2 mg of phenol and 1.3±0.1 mg of aluminum ions).

The problem stated is solved so that the method for producing the claimed preparation includes the preparation of a seed material of culture treponemes strains, the preparation of a microbial biomass in a liquid nutrient medium, concentration of the resulting microbial suspensions, the thermal inactivation of concentrated native suspensions, their preservation and purification. In the case of using several *Treponema pallidum* strains, it also includes mixing of the antigens obtained therefrom.

Various embodiments of the above process steps are possible. In one of the embodiments, when preparing inoculum, culture treponemal microbes are grown in meat-peptone broth with beef liver pieces under anaerobic conditions at a temperature of (37±1°) C during 7-10 days; to produce the microbial biomass, the culture treponemes are cultivated in the commercial liquid nutrient medium "Spirolate Broth, OMATA" with 10% commercial bovine serum added, or in an artificial thioglycolic medium (for example, manufactured according to RU 2,141,339) under anaerobic conditions at a temperature of (37±1°) C in a shaker-incubator at 120±10 rpm during 7-10 days; the concentration of the obtained microbial suspension of culture treponemes can be performed by natural deposition for 22-24 h and partial decantation of the supernatant (60 to 80% of the total volume of the culture liquid), for example, by means of a vacuum system; thermoinactivation of the concentrated native suspension of culture treponemes is performed once at a temperature of (58±2°) C for 60 min; the thermoinactivated concentrated suspensions of culture treponemes is performed by adding phenol to a final concentration of 0.5±0.1%; purification is carried out, for example, by filtration and subsequent washing with a physiological sodium chloride solution with the addition of phenol to a final concentration of 0.5±0.1%, which is made three times.

The corpuscular antigens of culture treponemes are prepared from the purified suspension with a required concentration (for example, at least 25 units of extinction, corresponding to 35 mg/ml of the microbial antigen in terms of dry matter). In a particular embodiment of the invention, corpuscular antigens are prepared from at least three cultural treponemes strains belonging to different antigenic groups, followed by their mixing (individual treponemes strains are mixed, for example, in equal proportions in several combinations such that at least one strain pertaining to one of the three antigenic groups will be present in the final polyvalent preparation).

To prepare the preparation, the calculated amounts of corpuscular antigen and phenolized sodium chloride physiological saline solution (0.25±0.02% phenol) are mixed in such a way that the final preparation for therapy contains a required amount of microbial antigen (for example, 0.5±0.1 mg/ml) in terms of dry matter. In another embodiment of the method, the calculated amounts of the polyvalent corpuscular antigen, the phenolized physiological saline solution of sodium chloride (0.25±0.02% phenol) and aluminum hydroxide (1.3±0.1 mg/ml aluminum ions) are mixed in such a way that the final preparation for prophylaxis contained a required amount of microbial antigen (e.g., 28.0±1.0 mg/ml) in terms of dry matter.

The stated problem is solved so that the method for modulating the antitumoral immunity comprises parenteral administering the claimed preparation of claim 1 (for example, as a subcutaneous injection) in a pharmaceutically acceptable amount. The method for the prevention or treatment of oncological diseases also includes parenteral administration of the preparation in a pharmaceutically acceptable amount. When cancer prevention, together with administration of the claimed preparation, additional administration of another preparation is possible, where the commercial live dry brucellosis vaccine is used as an active substance in a dose recommended by the official instruction for its use.

In embodiments of the invention on models of various tumors, the preparation was administered subcutaneously in a dose of 0.125 mg of antigen (dry matter) five times with a 1 day interval between the first four injections, a 14-day interval between the fourth and fifth injections; in order to prevent cancer, the preparation sorbed on aluminum hydroxide was subcutaneously administered in a dose of 7.0 mg of antigen (dry matter) once.

Our analysis of scientific information, patent literature and Internet resources has revealed that the most complete set of culture treponemes *pallidum* strains is available at Allergen (Stavropol, Russian Federation), a branch of the Research-Industrial Concern Microgen, where they are used in the manufacture of treponemal ultrasound-treated diagnosticum for a complement binding reaction.

Any compositions known in the art can be used as nutrient media for growing culture treponemes *pallidum*. To maintain cultures, traditional meat-peptone broth with boiled liver pieces added is used. For biomass accumulation, the commercial "Spirolate Broth, OMATA" (HiMedia Laboratories Pvt. Ltd., India), as well as the artificial thioglycolic medium disclosed in RU 2,141,339 can be used.

To provide anaerobic conditions, thioglycolic acid or its salts is added to the media, the native serum of horse, rabbit or cattle is added to stimulate the growth of the pathogen. The optimal growth of the pathogen in the liquid nutrient media can be observed on the 7-10$^{th}$ day of cultivation at a temperature of 37±1° C.

Studies of the efficacy of the claimed preparation on models of transplanted tumors such as melanoma, sarcoma, etc., which are commonly used in the evaluation of the efficiency of new antitumor preparations (Treschalina E. M. Antitumor activity of substances of natural origin.—Moscow, 2005, Rus; Manual on experimental (preclinical) study of new pharmacological substances (ed. R. U. Khabriev, Moscow, Medicine Press, 2005.—832 p, Rus) have shown a positive effect of the treponemal antigen on the growth and metastasis of malignant tumors. The results obtained are due to certain mechanisms mediated through the immune system that have common nonspecific features in the functioning of anti-infectious and antitumor immunity, which in this case develops according to the Th1-dependent type with the activation of cytotoxic T-lymphocytes, macrophages, the synthesis of a large number of various mediators by immunocompetent cells, which is also illustrated by the following examples. Some data of the research conducted are presented in the examples below, which do not limit the present invention, but only demonstrate the technical result achieved.

Within the framework of the present invention, the objectives of designing an antitumor preparation based on the causative agent of syphilis were solved by using *Treponema pallidum* culture strains.

Based on the results of the research conducted, it should be noted that the effect is achieved by using at least one *Treponema pallidum* strain as the main component, preferably by using not less than 3 treponemes *pallidum* culture strains belonging to at least 3 known antigenic groups in various combinations as a basis of the preparation (Zebnitskaya L. B. Vestnik dermatologii i venerologii, 1955, No. 4, p. 24-27 [Rus]). In particular, it is known that the IX Stavropol strain belongs to the first group; the VII and VIII Stavropol strains belong to the second one; the V Kazan strain and Reiter's strain belong to the third one, etc. In one embodiment of the invention, a polyvalent corpuscular antigen was prepared on the basis of concentrated native suspensions of the treponemes culture strains; in another one it was prepared on the basis of thermoinactivated suspensions of treponemes culture strains. As a result of the experiments, the effectiveness of the application of the claimed preparation as an immunostimulating preparation for the prevention and therapy of tumors was demonstrated.

Thus, the invention is based on the producing and use of a new preparation of microbial origin prepared from native or inactivated cells of treponemes *pallidum* culture strains. The preparation is characterized by a reproducible production technology, safety, high immunity-stimulating and antitumor efficacy in experiments on laboratory animals and transplanted tumor models.

The developed technology of producing of the preparation is based on a certain sequence of actions (stages) with the use of nutrient media, growing conditions, concentration, gentle inactivation, purification of microbial suspensions at certain stages, and provides the necessary quantities of the antigenic preparation of high immunogenicity (Table 1).

The use of a set of control indicators at all stages of the producing of the preparation (Table 2) ensures the reproducibility and standardization of the producing technology. The use of corpuscular treponemal antigen as an immunity-stimulating agent for parenteral administration to laboratory animals is characterized by a high immunity-stimulating effect on the indices of the cellular immunity and a pronounced antitumor effect when used on models of transplanted tumors.

Thus, the new preparation of microbial origin designed on the basis of culture treponemes *pallidum* and its use for the prevention and therapy of tumors are new and meet the inventive step criterion.

DETAIL DESCRIPTION OF EXAMPLES OF THE INVENTION

The invention is illustrated by the following examples.

Example 1. A Method of the Preparation a Polyvalent Corpuscular Inactivated Antigen Based on Treponemes Culture Strains The division of treponemes *pallidum* into 3 antigenic groups is known from the prior art. The treponemal strains of Reiter, V ($3^{rd}$ antigenic group), VII, VIII ($2^{nd}$ antigenic group), IX ($1^{st}$ antigenic group) in various combinations were used to prepare a polyvalent corpuscular inactivated antigenic preparation. The main stages of antigen preparation, check points and requirements for quality indicators are presented in Tables 1 and 2.

According to this scheme, 4 antigen preparation series were prepared, differing by a combination of the strains involved. Quality characteristics are presented in Table 3.

TABLE 1

Main stages of the preparation of a polyvalent corpuscular inactivated antigen based on treponemes culture strains

| Stage number | Stage name | Work content | Controlled indicators |
|---|---|---|---|
| 1 | Preparation of seed material of treponemes strains | Cultivation of microbes in meat-peptone broth with the addition of liver pieces under anaerobic static conditions at a temperature of $(37 \pm 1)°$ C. for 7-10 days with daily mixing | Nature of growth in the culture medium<br>Morphological properties in native "crushed drop" preparations<br>Extinction index<br>Presence of extraneous microflora |
| 2 | Preparation of native concentrated cultures of treponemes strains | Cultivation of microbes in a liquid nutrient medium with the addition of native serum under anaerobic conditions at $(37 \pm 1)°$ C. for 7-10 days in a shaker-incubator at a platform rotation speed of $120 \pm 10$ rpm.<br>Settling the culture liquid for 22-24 h at $(20 \pm 1)°$ C. to compact the deposit, concentrating it by partial decanting of the supernatant with a vacuum system. | Appearance<br>Morphological properties in native "crushed drop" preparations<br>Extinction index<br>Presence of extraneous microflora |
| 3 | Preparation of inactivated concentrated microbial suspensions of treponemes strains | One-time thermal inactivation of concentrated native suspensions at $(58 \pm 2)°$ C. for 60 min followed by preservation by the addition of phenol to a final concentration of $0.5 \pm 0.1\%$ and incubation at $(37 \pm 1)°$ C. for 22-24 h. | Appearance<br>General sterility<br>Specific sterility |
| 4 | Preparation of corpuscular antigens of treponemes strains | Threefold washing using centrifugation of inactivated concentrated suspensions of *treponemia* strains with phenolized ($0.5 \pm 0.1\%$ phenol) sodium chloride solution. Resuspension of the deposits in the calculated (by weight) amount of phenolized ($0.25 \pm 0.02\%$ phenol) saline solution. | Appearance<br>Presence of extraneous microflora<br>Extinction index |
| 5 | Preparation of polyvalent corpuscular antigen | Preparation of corpuscular antigens of treponemes strains with an optical density of suspension of at least 25 units of extinction. Mixing corpuscular antigens of strains in equal proportions in various combinations. | Appearance<br>General sterility<br>Specific activity in the diffusion precipitation reaction with the hyperimmune rabbit treponemal serum<br>Toxicity when administered to laboratory animals<br>Antigenic activity when administered subcutaneously to rabbits<br>Extinction index |
| 6 | Producing of preparations | The preparation intended for the evaluation of therapeutic efficacy is prepared by mixing the polyvalent corpuscular antigen and the phenolized ($0.25 \pm 0.02\%$ phenol) physiological solution in calculated proportions.<br>The preparation intended for the evaluation of preventive efficacy is prepared by mixing the polyvalent corpuscular antigen, the phenolized ($0.25 \pm 0.02\%$ phenol) physiological saline solution and an adjuvant (aluminum hydroxide gel), in the calculated proportions, taking into account the initial concentration of aluminum ions therein. | Appearance<br>pH value<br>Content of phenol<br>Content of corpuscular microbial antigen in terms of dry matter*<br>Content of aluminum ions**<br>General sterility<br>Toxicity when administered to laboratory animals<br>Specific activity in the diffusion precipitation reaction with the hyperimmune rabbit treponemal serum |

Notes
1 *The content of corpuscular microbial antigen for various experimental samples of the vaccine is determined in accordance with the calibration plot shown in FIG. 1.
2 **The indicator is determined for the preparation samples intended for the evaluation of preventive efficacy.
3 The medium for seed preparation is: peptone - 13.0 g/L; sodium chloride - 5.0 g/L; beef liver - 100.0 g/L; meat water - in the calculated volume, pH $8.2 \pm 0.2$.
4 The medium for obtaining a deep culture is: commercial "Spirolate Broth, OMATA" (HiMedia Laboratories Pvt. Ltd., India) is prepared according to the instructions attached, native bovine serum is additionally introduced in an amount of 10%; as well as the artificial thioglycolic medium disclosed in patent RU 2,141,339.

TABLE 2

Quality indicators of semi-finished products and final preparations obtained in the preparation of polyvalent corpuscular inactivated antigen on the basis of *treponema pallidum* culture strains

| Semi-finished product | Quality indicator (property) | Requirements for the indicator (property) |
|---|---|---|
| Seed cultures of treponemes strains | Growth pattern in the culture medium | Uniform clouding of the medium, a light gray deposit is formed with a prolonged standing, which is easily broken upon shaking |
| | Morphological properties in native "crushed drop" preparations | Typical mobile evenly convoluted thin spirochetes |
| | Value of the extinction index E, units of extinction | Not less than 0.4 |
| | Presence of extraneous microflora | Not allowed |
| Native concentrated cultures of treponemes strains | Appearance | Homogeneous grayish suspension, delaminates when stored |
| | Morphological properties in native "crushed drop" preparations | Typical mobile evenly convoluted thin spirochetes and an insignificant quantity of cysts |
| | Value of the extinction index E, units of extinction | Not less than 5.0 |
| | Presence of extraneous microflora | Not allowed |
| Inactivated concentrated microbial suspensions of treponemes strains | Appearance | Homogeneous grayish suspension, delaminates when stored, should not contain foreign impurities |
| | Specific sterility | Must not contain live treponemes |
| | General sterility | Must not contain extraneous microflora |
| Corpuscular antigens of treponemes strains | Appearance | Homogeneous grayish suspension, delaminates when stored, should not contain extraneous inclusions |
| | Presence of extraneous microflora | Not allowed |
| | Value of the extinction index E, units of extinction | Not less than 25.0 |
| Polyvalent corpuscular antigen | Appearance | Homogeneous grayish suspension, delaminates when stored, should not contain foreign impurities |
| | General sterility | Must not contain extraneous microflora |
| | Specific activity in the diffusion precipitation reaction with hyperimmune rabbit treponemal serum, antigenicity units/ml | Not less than 400 |
| | Toxicity when administered to laboratory animals | Atoxic (should not cause death, general and local reactions) |
| | Antigenic activity upon subcutaneous administration to rabbits | Titer of antibodies in the complement fixation reaction after 21 days after the administration of the preparation 1:160, not less than |
| | Value of the extinction index E, units of extinction | Not less than 25.0 |
| Preparations | Appearance | Homogeneous grayish suspension, delaminates when stored, should not contain foreign impurities (nonspecific impurities and flakes) |
| | pH value, units of pH | 6.6 to 7.0 |
| | Content of phenol, mg/ml | 2.3 to 2.7 |
| | Content of corpuscular microbial antigen in terms of dry matter, mg/ml | 27.0-29.0 for the prophylactic preparation; 0.4-0.6 for the medicinal product* |
| | Content of aluminum ions, mg/ml | 1.2 to 1.4** |
| | General sterility | Must not contain extraneous microflora |
| | Toxicity when administered to laboratory animals | Atoxic (should not cause death, general and local reactions, weight loss) |
| | Specific activity in the diffusion precipitation reaction with hyperimmune rabbit treponemal serum, antigenicity units/ml | Not less than 400 |

Notes.
1 *The content of corpuscular microbial antigen for various experimental samples of the vaccine was determined in accordance with the calibration plot shown in FIG. 1.
2 **The indicator is determined for the samples of the preparation intended for the evaluation of preventive efficacy.

TABLE 3

Quality characteristics of polyvalent corpuscular inactivated antigens prepared on the basis of various combinations of treponemes culture strains

| Characteristic, property | Conditionality requirements | Characteristics of the indicator (property description) for a combination of strains | | | |
|---|---|---|---|---|---|
| | | 1 | 2 | 3 | 4 |
| Appearance | Homogeneous grayish suspension, delaminates when stored, must not contain foreign impurities | Homogeneous grayish suspension, delaminates when stored, contains no foreign impurities | Homogeneous grayish suspension, delaminates when stored, contains no foreign impurities | Homogeneous grayish suspension, delaminates when stored, contains no extraneous inclusions | Homogeneous grayish suspension, delaminates when stored, contains no extraneous inclusions |
| General sterility | Must not contain foreign microflora | Does not contain extraneous microflora | Does not contain extraneous microflora | Does not contain extraneous microflora | Does not contain extraneous microflora |

TABLE 3-continued

Quality characteristics of polyvalent corpuscular inactivated antigens prepared
on the basis of various combinations of treponemes culture strains

| Characteristic, property | Conditionality requirements | Characteristics of the indicator (property description) for a combination of strains | | | |
|---|---|---|---|---|---|
| | | 1 | 2 | 3 | 4 |
| Specific activity in the diffusion precipitation reaction with hyperimmune rabbit treponemal serum, antigenicity units/ml | Not less than 400 | 650 | 600 | 600 | 650 |
| Toxicity when administered to laboratory animals | Atoxic (should not cause death, general and local reactions) | Atoxic | Atoxic | Atoxic | Atoxic |
| Antigen content in terms of dry matter, mg | Not less than 35.0 | 38.0 | 40.0 | 36.0 | 35.0 |

Notes:
1 - a combination of strains IX + VII + V; 2 - a combination of strains IX + VII + Reiter's; 3 - a combination of strains IX + VIII + V; 4 - a combination of strains IX + VIII + Reiter's.

Thus, the use of at least 3 treponemes *pallidum* culture strains belonging to the known 3 antigenic groups in various combinations in the composition of the presented samples provides full antigenic value, representativeness and homology of the preparation with respect to pathogenic tissue treponemes.

Example 2. A Method for Producing a Polyvalent Corpuscular Native Antigen Based on Laboratory Treponemes Strains To obtain a polyvalent corpuscular native antigenic preparation, the treponemes strains of Reiter, V ($3^{rd}$ antigenic group), VII, VIII ($2^{nd}$ antigenic group), IX ($1^{st}$ antigenic group) were used in various combinations. The main stages of antigen preparation, check points and requirements for quality indicators are presented in Tables 4 and 5.

According to this scheme, 4 antigen preparation series were prepared, differing by a combination of the strains involved. Quality characteristics are presented in Table 6.

TABLE 4

Main stages of the preparation of a polyvalent corpuscular native antigen on the basis of treponemes culture strains

| Stage number | Stage name | Work content | Controlled indicators |
|---|---|---|---|
| 1 | Preparation of seed material of treponemes strains | Cultivation of microbes in meat-peptone broth with the addition of liver pieces under anaerobic static conditions at (37 ± 1)° C. for 7-10 days with daily mixing | Nature of growth in the culture medium<br>Morphological properties in native "crushed drop" preparations<br>Value of the extinction index<br>Presence of extraneous microflora |
| 2 | Preparation of native concentrated cultures of treponemes strains | Cultivation of microbes in a liquid nutrient medium with the addition of native serum under anaerobic conditions at (37 ± 1)° C. for 7-10 days in a shaker-incubator with a rotation speed of 120 ± 10 rpm<br>Settling the culture liquid for 22-24 h at (20 ± 1)° C. to compact the deposit, concentrating by partial decanting of the supernatant with a vacuum system. | Appearance<br>Morphological properties in native "crushed drop" preparations<br>Value of the extinction index<br>Presence of extraneous microflora |
| 3 | Preparation of corpuscular antigens of treponemes strains | Triple washing using centrifugation of native concentrated suspensions of treponemes strains with a sodium chloride solution.<br>Resuspension of the deposit in the calculated (by weight) amount of physiological sodium chloride solution. | Appearance<br>Presence of extraneous microflora<br>Value of the extinction index |
| 4 | Preparation of polyvalent corpuscular antigen | Preparation of corpuscular antigens of treponemes strains with an optical density of suspension of at least 25 units of extinction.<br>Mixing corpuscular antigens of strains in equal proportions in various combinations. | Appearance<br>Value of the extinction index |

TABLE 4-continued

Main stages of the preparation of a polyvalent corpuscular native antigen on the basis of treponemes culture strains

| Stage number | Stage name | Work content | Controlled indicators |
| --- | --- | --- | --- |
| 5 | Producing of preparations | The preparation intended for the evaluation of therapeutic efficacy is prepared by mixing polyvalent corpuscular antigen and a physiological sodium chloride solution in the calculated proportions | Appearance Content of corpuscular microbial antigen in terms of dry matter* |

Notes.
1 *The content of corpuscular microbial antigen for various experimental samples of the vaccine is determined in accordance with the calibration plot shown in FIG. 1.
2 **The indicator is determined for the samples of the preparation intended for the evaluation of preventive efficacy.
3 The medium for seed preparation is: peptone - 13.0 g/L; sodium chloride - 5.0 g/L, beef liver - 100.0 g/L; meat water - in the calculated volume, pH 8.2 ± 0.2.
4 The medium for obtaining a deep culture is: the commercial "Spirolate Broth, OMATA" (HiMedia Laboratories Pvt. Ltd., India), prepared according to the attached instructions, native bovine serum is additionally introduced in an amount of 10%; as well as the artificial thioglycolic medium disclosed in patent RU 2,141,339.

TABLE 5

Quality indicators of semi-finished products and final preparations obtained in the preparation of polyvalent corpuscular native antigen on the basis of *treponema pallidum* culture strains

| Semi-finished product | Quality indicator (property) | Requirements for the indicator (property) |
| --- | --- | --- |
| Seed cultures of treponemes strains | Growth pattern in the culture medium | Uniform clouding of the medium, a light gray deposit is formed upon a prolonged standing, which is easily broken upon shaking |
| | Morphological properties in native "crushed drop" preparations | Typical mobile evenly convoluted thin spirochetes |
| | Value of the extinction index E, units of extinction | Not less than 0.4 |
| | Presence of extraneous microflora | Not allowed |
| Native concentrated cultures of treponemes strains | Appearance | Homogeneous grayish suspension, delaminates when stored |
| | Morphological properties in native "crushed drop" preparations | Typical mobile evenly convoluted thin spirochetes and insignificant quantity of cysts |
| | Value of the extinction index E, units of extinction | Not less than 5.0 |
| | Presence of extraneous microflora | Not allowed |
| Corpuscular antigens of treponemes strains | Appearance | Homogeneous grayish suspension, delaminates when stored, should not contain extraneous inclusions |
| | Presence of extraneous microflora | Not allowed |
| | Value of the extinction index E, units of extinction | Not less than 15.0 |
| Polyvalent corpuscular antigen | Appearance | Homogeneous grayish suspension, delaminates when stored, should not contain foreign impurities |
| | Value of the extinction index E, units of extinction | Not less than 15.0 |
| Preparations | Appearance | Homogeneous grayish suspension, delaminates when stored, should not contain foreign impurities (nonspecific impurities and flakes) |
| | Content of corpuscular microbial antigen in terms of dry matter, mg/ml | 0.4 to 0.6* |

Notes.
1 *The content of corpuscular microbial antigen for various experimental samples of the vaccine was determined in accordance with the calibration plot shown in FIG. 1.
2 **The indicator is determined for the samples of the preparation intended for the evaluation of preventive efficacy.

TABLE 6

Quality characteristics of polyvalent corpuscular native antigens prepared on the basis of various combinations of treponemes culture strains

| Characteristic, property | Requirements for conditionality | Characteristics of the indicator (property description) for combinations of strains | | | |
| --- | --- | --- | --- | --- | --- |
| | | 1 | 2 | 3 | 4 |
| Appearance | Homogeneous grayish suspension, delaminates when stored, must not contain foreign impurities | Homogeneous grayish suspension, delaminates when stored, contains no foreign impurities | Homogeneous grayish suspension, delaminates when stored, contains no foreign impurities | Homogeneous grayish suspension, delaminates when stored, contains no extraneous inclusions | Homogeneous grayish suspension, delaminates when stored, contains no extraneous inclusions |

TABLE 6-continued

Quality characteristics of polyvalent corpuscular native antigens prepared on the basis of various combinations of treponemes culture strains

| Characteristic, property | Requirements for conditionality | Characteristics of the indicator (property description) for combinations of strains | | | |
|---|---|---|---|---|---|
| | | 1 | 2 | 3 | 4 |
| Antigen content in terms of dry matter, mg | Not less than 20.0 | 28.0 | 30.0 | 24.0 | 25.0 |

Note:
1 - a combination of strains IX + VII + V; 2 - a combination of strains IX + VII + Reiter's; 3 - a combination of strains IX + VIII + V; 4 - a combination of strains IX + VIII + Reiter's.

Example 3. Characteristics of the Nonspecific Immunity-Stimulating Effect of the Polyvalent Antigen on the Basis of Culture Treponemes Strains on the T-Cell Immunity Indices The nonspecific immunity-stimulating effect of the polyvalent corpuscular treponemal antigen on the cellular immunity indices was evaluated in nonlinear white mice. The preparation was administered to the animals subcutaneously in a single dose of 0.125 mg of antigen (dry matter) five times at 1-day intervals. The immunity stimulation indices were evaluated on days 14 and 21 after administration.

In the experiments, the stimulating effect of the preparation on the relative (fraction) and absolute content (cells/ml) of lymphocyte populations (subpopulations) was studied, which have the main role in the antitumor immunity. Traditional CD markers were used in order to differentiate individual pools of lymphocytes. Quantitative estimation of the lymphocyte subpopulations was carried out using a flow cytofluorimeter Navios (Beckman Coulter, USA).

When assessing the dynamics of the cellular immunity indices, the stimulation coefficient (SC) was used to visualize information, which was calculated by the formula:

$$SC = (A_2 - A_1) : A_1 \cdot 100 \quad (1);$$

where:

$A_1$ is the absolute (relative) background value of the indicator; and $A_2$ the absolute (relative) value of the indicator after the preparation administration.

The results of the studies are presented in Tables 7 and 8.

TABLE 7

Dynamics of the populations (subpopulations) of lymphocytes in blood of mice after five-fold administration of polyvalent corpuscular treponemal antigen in a total dose of 0.625 mg of antigen

| Markers of populations (subpopulations) | Relative content of lymphocyte populations (subpopulations) in ... days from the beginning of the course, %, X + I$_{95}$, N = 5 | | | Absolute content of lymphocyte populations (subpopulations) in ... days from the beginning of the course, billion/L | | |
|---|---|---|---|---|---|---|
| | 0 (background) | 14 | 21 | 0 (background) | 14 | 21 |
| Leukocytes | 95.0 ... 100.0 | 95.0 ... 100.0 | 95.0 ... 100.0 | 8.000 ± 0.9 | 31.000 ± 1.9 | 9.367 ± 2.0 |
| Lymphocytes | 59.9 ± 6.9 | 58.8 ± 6.5 | 59.1 ± 11.7 | 4.792 | 16.368 | 5.536 |
| $CD_3^+$ | 54.6 ± 5.5 | 55.6 ± 5.7 | 56.3 ± 3.1 | 2.616 | 8.610 | 2.951 |
| $CD_8^+$ | 22.6 ± 2.3 | 22.7 ± 2.2 | 22.6 ± 2.0 | 0.591 | 1.868 | 0.626 |
| $CD_4^+$ | 77.4 ± 2.3 | 78.3 ± 2.2 | 78.8 ± 2.0 | 2.025 | 6.741 | 2.325 |
| $NK^+$ | 0.8 ± 0.3 | 1.3 ± 0.5 | 1Д. ± 0.5 | 0.040 | 0.213 | 0.047 |
| $CD_4^+IFN\text{-}\gamma^+$ | 2.1 ± 0.3 | 7.0 ± 2.2 | 6.1 ± 2.0 | 0.043 | 0.372 | 0.142 |
| $CD_8^+IFN\text{-}\gamma^+$ | 13.6 ± 2.6 | 24.9 ± 3.1 | 20.9 ± 3.9 | 0.080 | 0.465 | 0.131 |
| $NK^+IFN\text{-}\gamma^+$ | 5.6 ± 2.6 | 16.9 ± 7.4 | 6.7 ± 3.7 | 0.002 | 0.036 | 0.003 |

Notes.

1 $CD_3^+$ is the marker of T cells;

2 $CD_8^+$ the marker of cytotoxic T lymphocytes;

3 $CD_4^+$ the common marker of T helper cells;

4 $NK^+$ the marker of natural killers;

5 $CD_4^+IFN\text{-}\gamma^+$ the marker of T helper lymphocytes producing interferon γ;

6 $CD_8^+IFN\text{-}\gamma^+$ the marker of cytotoxic T lymphocytes producing interferon γ;

7 $NK^+IFN\text{-}\gamma^+$ the marker of natural killers producing interferon γ.

TABLE 8

Dynamics of the cellular immunity indices according to the stimulation coefficient of the populations
(subpopulations) of lymphocytes in the blood of mice after five-fold administration of corpuscular
inactivated antigen from treponemes culture strains at a dose of 0.625 mg of antigen

| Markers of populations (subpopulations) | Value of the stimulation coefficient of the relative content of populations (subpopulations) of lymphocytes in . . . days from the beginning of the course | | Value of the stimulation coefficient of the absolute content of populations (subpopulations) of lymphocytes in . . . days from the beginning of the course | |
|---|---|---|---|---|
| | 14 | 21 | 14 | 21 |
| Lymphocyte fraction among leukocytes | −1.8 | −1.3 | 241.6 | 15.5 |
| $CD_3^+$ | 1.8 | 3.1 | 229.1 | 12.8 |
| $CD_8^+$ | 0.4 | 1.0 | 216.1 | 5.9 |
| $CD_4^+$ | 1.2 | 1.8 | 232.9 | 30.0 |
| $NK^+$ | 62.5 | 37.5 | 432.5 | 17.5 |
| $CD_4^+IFN\text{-}\gamma^+$ | 233.3 | 190.5 | 765.1 | 38.9 |
| $CD_8^+IFN\text{-}\gamma^+$ | 83.1 | 53.7 | 481.3 | 63.8 |
| $NK^+IFN\text{-}\gamma^+$ | 201.8 | 19.6 | 1700.0 | 50.0 |

Notes.
1 $CD_3^+$ is the marker of T lymphocytes;
2 $CD_8^+$ the marker of cytotoxic T lymphocytes;
3 $CD_4^+$ the common marker of T helper cells;
4 NK the marker of natural killers;
5 $CD_4^+IFN\text{-}\gamma^+$ the marker of T helper cells of producing interferon γ;
6 $CD_8^+IFN\text{-}\gamma^+$ the marker of cytotoxic T lymphocytes producing interferon γ;
7 $NK^+IFN\text{-}\gamma^+$ the marker of natural killers producing interferon γ.

During the whole period of observation, stimulation of the indices of antitumoral cellular immunity was noted, which was manifested itself in an increased content of NK cells, T helper cells and cytotoxic T-lymphocytes, an increased level of INF-γ production by T helper cells and T suppressor cells. The maximum stimulation of these indices was observed on the $14^{th}$ day from the beginning of therapy, their values decreased by the $21^{st}$ day of observation, however, they exceeded the background ones.

Example 4. Therapy of Linear Mice with Grafted Tumor Strain of Melanoma B16 with the Claimed Preparation To evaluate the therapeutic efficiency of the preparation against solid tumors (of mesenchymal origin), an experiment was performed on a transdermal subcutaneous murine tumor strain of melanoma B16. C57BL/6 mice of both sexes were used in the experiment. The tumor was transplanted by subcutaneous injection into the region of the forelimb closer to the spine in a volume of 0.2 ml (200 thousand cells) per mouse. One group of animals was administered the multivalent antigen based on cultural treponemes subcutaneously in 1, 3, 5, 7, and 14 days after implantation of the tumor with therapeutic purposes in a single dose of 0.125 mg. The second group of animals was injected the preparation sorbed on aluminum hydroxide subcutaneously in a single dose of 0.625 mg once 1 day after implantation of the tumor.

As a control group, mice of the same line were used without administration of the preparation.

The antitumor effect was evaluated according to the following generally accepted indicators: tumor growth inhibition (TGI), the increase in lifespan (ILS), and metastatic inhibition index (MII).

The tumor growth inhibition index was calculated as follows. Starting from 12-14 days from the tumor implantation moment, 3 measurements of tumor nodes were performed every 5-7 days (depending on the tumor growth intensity). For this purpose, two sizes (length and width) of the tumor nodes were measured with a caliper. The volume (V, $mm^3$) was calculated by the formula:

$$V=(a \cdot b^2):2 \qquad (3);$$

where:
a is the length of the tumor node, mm, and
b the width of the tumor node, mm.
The tumor growth inhibition (TGI) index was calculated by the formula:

$$TGI=(V_{control}-V_{exper}):V_{control} \cdot 100\% \qquad (4);$$

where:
TGI is the tumor growth inhibition index, %;
$V_{control}$ the average tumor volume in the control group, $mm^3$; and
$V_{exper}$ the average tumor volume in the experimental group, $mm^3$.

The increase in lifespan (ILS) was calculated by the formula:

$$ILS=(ALS_{exper}-ALS_{control}):ALS_{control} \cdot 100\% \qquad (5);$$

Where
$ALS_{exper}$ is the average lifespan of the animals in the experimental group, days; and
$ALS_{control}$ the average lifespan of the animals in the control group, days.

The effect on the tumor's metastatic activity was studied in accordance with the procedure given below. In each experimental group, 5 mice were sacrificed on the day of death of the first mouse in the control group. The thoracic cavity of the animals was opened, the lungs were extracted, and the number of metastases was counted. The tumor metastasis frequency was calculated as the percentage of the number of animals with metastases to the total number of animals in the group. The average number of metastases per animal in the group was calculated. The metastatic inhibition index (MII) was calculated by the formula:

$$MII=(A_1B_1-A_2B_2):(A_1B_1) \cdot 100\% \qquad (6);$$

where:

$A_1$ is the frequency of metastasis in the control group;

$A_2$ the frequency of metastasis in the experimental group;

$B_1$ the average number of metastases in animals in the control group; and $B_2$ the average number of metastases in animals in the experimental group.

The results of the experiment are given in Table 9.

As follows from the data presented in the table, inhibition of tumor growth was noted for all observation periods (the maximum value of the TGI index was recorded on the 23$^{rd}$ day of observation and amounted to 40.2%) and a significant decrease in the level of metastasis (the MII value was 68.1%) in animals received the preparation on the basis of cultural treponemes strains according to the above scheme. No significant effect on the lifespan of the treated animals as compared to untreated ones was noted in the experiment.

When evaluating the effectiveness of the use of the preparation sorbed on aluminum hydroxide gel, a significant antitumor efficacy was established for the B16 melanoma model, which is higher than that of the unabsorbed preparation. The maximum TGI values were 61.7% and 40.2%, respectively. Besides the increase in the TGI and MII values, a significant increase in the lifespan of animals was observed in this experiment (the ILS index was 45.3% vs. minus 5.0% with 5-fold administration of the non-absorbed preparation).

Example 5. Therapy of Mice with Grafted Tumor Strain of Sarcoma Sa37 with the Claimed Preparation To evaluate the therapeutic efficacy of the preparation against solid tumors (of mesenchymal origin), an experiment was performed on a transdermal subcutaneous murine tumor strain of the Sa37 sarcoma. Balb/c mice of both sexes were used in the experiment.

The tumor was transplanted by subcutaneous injection into the region of the forelimb closer to the spine in a volume of 0.2 ml (300 thousand cells) per mouse. One group of animals was subcutaneously administered the polyvalent corpuscular treponemal antigen with therapeutic purposes at 1, 3, 5, 7, and 14 days after implantation of the tumor in a single dose of 0.125 mg. The second group of animals was subcutaneously injected the preparation sorbed on aluminum hydroxide in a single dose of 0.625 mg once in 1 day after implantation of the tumor.

Mice of the same line without administration of the preparation were used as a control group.

The antitumor effect was evaluated according to the following generally accepted indices: tumor growth inhibition (TGI) and the increase in lifespan (ILS). The procedure for calculating the indices is given in Example 4.

The data presented in Table 10 indicate that on the 12$^{th}$ and 17$^{th}$ day of observation, inhibition of tumor growth was noted in the group of animals receiving a five-fold injection of the preparation (the TGI values were 10.9% and 26.8%, respectively).

The results of the evaluation of the effectiveness of the use of the preparation sorbed on aluminum hydroxide gel, according to the curative scheme, showed no increase in the antitumor activity in comparison with the non-absorbed preparation.

TABLE 9

Evaluation of the therapeutic antitumor activity of polyvalent corpuscular inactivated antigen from treponemes culture strains using a tumor model of melanoma B16

| Preparation administration scheme | Dose of antigen administered in terms of dry matter, mg | | Quantity of animals | TGI in ... days after implantation, % | | | ILS, % | Fraction of animals with metastases, % | MII, % |
|---|---|---|---|---|---|---|---|---|---|
| | Single | Total | | 12 | 17 | 23 | | | |
| Five times: on days 1, 3, 5, 7, 14 days after grafting of the tumor strain | 0.125 | 0.625 | 21 | 26.8 | 38.6 | 40.2 | −5.0 | 33.3 | 68.1 |
| Once, the preparation sorbed on aluminum hydroxide gel after 1 day after grafting of the tumor strain | 0.625 | 0.625 | 12 | 61.7 | 49.6 | 44.0 | 45.3 | 30.0 | 71.3 |

Notes:
1 Mice were implanted with the tumor culture in a dose of 200,000 cells subcutaneously.
2 TGI is tumor growth inhibition.
3 ILS is the increase in lifespan.
4 MII is metastasis inhibition index.

TABLE 10

Evaluation of the antitumor activity of polyvalent corpuscular inactivated antigen from treponemes culture strains using a tumor model of sarcoma Sa37

| Preparation administration scheme | Dose of antigen administered in terms of dry matter, mg | | Quantity of animals | TGI index in . . . days after implantation, % | | ILS index, % |
|---|---|---|---|---|---|---|
| | Single | Total | | 12 | 17 | |
| Five times: on days 1, 3, 5, 7, 14 days after grafting of the tumor strain | 0.125 | 0.625 | 15 | 10.9 | 26.8 | −6.1 |
| Once, the preparation sorbed on aluminum hydroxide gel after 1 day after grafting of the tumor strain | 0.625 | 0.625 | 12 | 14.6 | 21.1 | −5.4 |

Notes:
1 Mice were implanted with the tumor culture at a dose of 300 thousand cells subcutaneously.
2 TGI is tumor growth inhibition.
3 ILS is the increase in lifespan.

Example 6. Combined Application of the Claimed Preparation and Commercial Brucellosis Live Powder Vaccine to Prevent Tumor Growth in a Mouse Experiment Using Transplantable Strains of Melanoma B16 and Sarcoma Sa37

To evaluate the antitumor efficacy of the preparation based on the *Treponema pallidum* culture strains in combination with the brucellosis live vaccine, an experiment was performed on transdermally subcutaneously murine tumor strains of melanoma B16 and sarcoma Sa37. C57BL/6 mice of both sexes (for melanoma) and Balb/c of both sexes (for sarcoma) were used in the experiment. The tumor was transplanted by subcutaneous injection into the forelimb region closer to the spine in a volume of 0.2 ml (200 thousand tumor cells of melanoma strain B16 and 300 thousand cells of sarcoma strain Sa37) per mouse. The schemes and doses of combined administration of the preparations are presented in Tables 11 and 12. Suspensions of cells of transplanted tumor strains were implanted in 45 days after the last administration of the vaccines.

Mice of the same line without administration of the preparation were used as a control group.

The antitumor effect was evaluated according to the following generally accepted indices: tumor growth inhibition (TGI) and the increase in lifespan (ILS). The procedure for calculating the indices is given in Example 4.

Analysis of the data presented in Tables 11 and 12 (implantation of tumor material in 45 days after the last administration of the preparation combination) in comparison with the results of the study of the efficiency of monotherapy of the claimed preparation (Tables 9 and 10) showed an increased antitumor efficacy when the combined use of the multivalent treponemal antigen and the brucellosis vaccine.

This effect was more pronounced on the B16 melanoma model, and less on the Sa37 sarcoma model. The maximum value of the TGI index was 73.6% and 47.0% for melanoma B16 and sarcoma Sa37, respectively, the ILS index was 13.5% and 29.2% for melanoma B16 and sarcoma Sa37, respectively. The maximum value of the MII index for melanoma B16 was 56.7%. The best effect was achieved on both models using the scheme of combined use: initially the animals were injected with the multivalent corpuscular inactivated antigenic preparation sorbed on aluminum hydroxide based on treponemes in a dose of 7.0 mg, and after 3 days they were injected the brucellosis live vaccine in a dose according to the instructions for subcutaneous injection, which is 400 million cells per mouse.

This scheme of combined application can be used to prevent (inhibit) tumor growth in high-risk groups.

TABLE 11

Evaluation of the antitumor activity of polyvalent corpuscular inactivated antigen from treponemes culture strains in combination with the brucellosis live vaccine using a tumor model of melanoma B16, $X_{mean} \pm I_{95}$

| Preparation administration scheme | Quantity of animals | TGI index in . . . days after implantation, % | | | ILS, % | Percentage of animals with metastases | MII, % |
|---|---|---|---|---|---|---|---|
| | | 14 | 20 | 28 | | | |
| Live brucellosis vaccine at a dose of 400 million cells subcutaneously, treponemal antigen sorbed on aluminum hydroxide at a dose of 7.0 mg after 3 days. | 10 | 73.6 | 55.2 | 53.7 | 13.5 | 70.0 | −7.8 |
| Treponemal antigen sorbed on aluminum hydroxide at a dose of 7.0 mg, live brucellosis vaccine at a dose of 400 million cells subcutaneously after 3 days | 10 | 66.0 | 46.4 | 60.0 | 7.2 | 50.0 | 56.7 |

TABLE 11-continued

Evaluation of the antitumor activity of polyvalent corpuscular inactivated antigen from treponemes culture strains in combination with the brucellosis live vaccine using a tumor model of melanoma B16, $X_{mean} \pm I_{95}$

| Preparation administration scheme | Quantity of animals | TGI index in . . . days after implantation, % | | | ILS, % | Percentage of animals with metastases | MII, % |
|---|---|---|---|---|---|---|---|
| | | 14 | 20 | 28 | | | |
| Simultaneous administration of the live brucellosis vaccine at a dose of 400 million cells subcutaneously and treponemal antigen sorbed on aluminum hydroxide at a dose of 7.0 mg of antigen | 9 | 51.7 | 31.6 | 41.9 | 9.8 | 44.4 | 20.8 |

Notes:
1 The tumor was implanted in a dose of 200 thousand cells subcutaneously after 45 days after the last injection of the vaccines.
2 TGI is tumor growth inhibition.
3 ILS is the increase in lifespan.

TABLE 12

Evaluation of the antitumor activity of polyvalent corpuscular inactivated antigen from treponemes culture strains in combination with brucellosis live vaccine using a tumor model of sarcoma Sa37, $X_{mean} \pm I_{95}$

| Preparation administration scheme | Quantity of animals | TGI index in . . . days after implantation, % | | | ILS, % |
|---|---|---|---|---|---|
| | | 14 | 20 | 28 | |
| Live brucellosis vaccine at a dose of 400 million cells subcutaneously treponemal antigen, sorbed on aluminum hydroxide at a dose of 7.0 mg after 3 days | 8 | 4.9 | 13.6 | 5.3 | −9.3 |
| Treponemal antigen sorbed on aluminum hydroxide at a dose of 7.0 mg, live brucellosis vaccine at a dose of 400 million cells subcutaneously after 3 days | 9 | 35.7 | 47.0 | 24.9 | 29.2 |
| Simultaneous administration of live brucellosis vaccine at a dose of 400 million cells subcutaneously and treponemal antigen sorbed on aluminum hydroxide at a dose of 7.0 mg of antigen | 10 | 24.2 | 22.7 | 29.6 | −17.6 |

Notes:
1 The tumor was implanted in a dose of 300 thousand cells subcutaneously after 45 days after the last injection of the vaccines.
2 TGI is tumor growth inhibition.
3 ILS is the increase in lifespan.

Example 7. Therapy of Mice with a Grafted Tumor Strain of Lewis Lung Carcinoma (LLC) with the Claimed Preparation To evaluate the therapeutic efficacy of the preparation against Lewis lung carcinoma, male C57BL/6 mice were used. The tumor was transplanted by subcutaneous injection into the region of the forelimb closer to the spine in a volume of 0.5 ml (1 million cells) per mouse. The polyvalent corpuscular antigen based on cultural treponemes was subcutaneously injected into one group of animals for therapeutic purposes at 1, 3, 5, 7, and 14 days after implantation of the tumor in a single dose of 0.125 mg. The second group of animals was injected the preparation sorbed on aluminum hydroxide subcutaneously in a single dose of 0.625 mg once in 1 day after implantation of the tumor.

Mice of the same line with an implanted tumor without administration of the test preparation were used as a control group.

The antitumor effect was assessed according to the following generally accepted indices: tumor growth inhibition (TGI), the increase in lifespan (ILS) and metastatic inhibition index (MII). The procedure for calculating the indices is given in Example 4.

The data presented in Table 13 indicate that with a five-fold administration of the polyvalent antigen, some (about 13%) inhibition of tumor growth occurred with no significant increase in the life duration of the animals.

The results of the evaluation of the effectiveness of using the preparation sorbed on aluminum hydroxide gel according to the curative scheme indicate that this method of treatment leads to inhibition of tumor growth in the range of 18-24% and a decrease in metastasis (MII=17.6%).

TABLE 13

Evaluation of the antitumor activity of corpuscular inactivated antigen from treponemes culture strains using a tumor model of Lewis carcinoma (LLC), $X_{mean} \pm I_{95}$

| Preparation administration scheme | Dose of antigen administered in terms of dry matter, mg | | Number of animals | TGI index in . . . days after implantation, % | | | ILS, % | Percentage of animals with metastases | MII, % |
|---|---|---|---|---|---|---|---|---|---|
| | Single | Total | | 12 | 17 | 23 | | | |
| Five times: on days 1, 3, 5, 7, 14 days after grafting of the tumor strain | 0.125 | 0.625 | 15 | 4.2 | 5.3 | 13.2 | −3.0 | 33.3 | 12.1 |
| Once, the preparation sorbed on aluminum hydroxide gel 1 day after grafting of the tumor strain | 0.625 | 0.625 | 15 | 18.0 | 21.7 | 24.3 | −3.1 | 23.6 | 17.6 |

Notes:
1 Mice were implanted with the tumor culture in a dose of 1 million cells subcutaneously.
2 TGI is tumor growth inhibition.
3 ILS is the increase in lifespan.

Example 8. Therapy of Rabbits with a Grafted Tumor Strain of the Brown-Pierce Carcinoma with the Claimed Preparation To assess the preventive efficacy of the preparation against Brown-Pierce carcinoma, male rabbits of the Giant breed were used.

The tumor was transplanted by injecting a tumor tissue into the testicle. For this, the tumor node was gently homogenized in a sterile mortar with a small amount of sterile 0.9% sodium chloride saline solution and filtered through 2 layers of gauze to remove large pieces of tumor tissue. 0.5 ml of a 20% suspension of tumor cells was taken for injection.

The animals were injected with the polyvalent corpuscular inactivated antigen based on cultural treponemes, sorbed on aluminum hydroxide, in a dose of 28 mg of antigen (dry matter) once. A month after the administration of the preparation, an intratesticular inoculation of the Brown-Pierce carcinoma was performed. Rabbits of the same breed with an implanted tumor without administration of the test preparation were used as a control group.

The antitumor effect was evaluated according to the following generally accepted indices: tumor growth inhibition (TGI) and the increase in lifespan (ILS). The procedure for calculating the indices is given in Example 4.

The data presented in Table 14 indicate that, upon administration of the test preparation sorbed on aluminum hydroxide gel by the prophylactic scheme, Brain-Pierce carcinoma inhibition on the 30$^{th}$ and 60$^{th}$ day of the experiment was observed in a range of 20-25%, while the ILS of the experimental animals increased by 30%.

TABLE 14

Evaluation of the antitumor activity of polyvalent corpuscular inactivated sorbed antigen based on culture treponemes using the Brown-Pierce carcinoma tumor model

| Preparation administration scheme | Dose of antigen administered in terms of dry matter, mg | | Number of animals | TGI index in . . . days after implantation, % | | ILS, % |
|---|---|---|---|---|---|---|
| | Single | Total | | 30 | 60 | |
| Once, the preparation sorbed on aluminum hydroxide gel | 28.0 | 28.0 | 7 | 18.6 | 25.3 | 30.0 |

Notes:
1 Rabbits were implanted with the tumor culture in a dose of 0.5 ml of a 20% suspension of tumor cells intratesticularly.
2 TGI is tumor growth inhibition.
3 ILS is the increase in lifespan.
4 "-" the indicator was not evaluated.

Thus, the claimed preparation has a nonspecific immunity-stimulating action with a predominant effect on the T-cell immunity. The preparation when therapeutic use effectively affects tumors of various histogenesis.

Example 9. Characteristics of the Nonspecific Immunity-Stimulating Effect of the Polyvalent Antigen on the Basis of Culture Treponemes Strains Against the Heterologous Pathogen *Salmonella typhimurium*

The intensity of heterologous immunity against the background of immunization with experimental samples of the vaccine was evaluated on white mice of both sexes weighing 18.0-20.0 g.

The animals were subcutaneously immunized with the preparation sorbed on aluminum hydroxide in a volume of 0.5 ml twice with an interval of 14 days in a dose of 3.5 mg of the corpuscular microbial antigen (dry matter). The LD50 value for the culture of the *Salmonella typhimurium* strain was subsequently evaluated in the immunized and control group using the subgroup method.

For this purpose, after 60 days after the administration of the preparation, the mice were subcutaneously infected with multiple doses of a microbial suspension prepared from an agar culture of *S. typhimurium* strain. A total of 5 doses were used in the experiment. 6 intact and 6 immunized animals were infected with each dose. The mice were observed for 14 days and the presence and timing of animal deaths were recorded by groups. Specificity of death was confirmed bacteriologically.

At the end of the observation, the value LD50 was calculated for the control and immunized group by the Kerber method in the Ashmarin modification:

$$1 \text{ g LD}_{50} = 1 \text{ g } D_{max} - \delta \cdot (\Sigma Li - 0.5) \qquad (2);$$

where:
$LD_{50}$ is the dose that causes death of 50% of animals;
$\delta$ the logarithm of the dilution multiplicity;
$D_{max}$ the maximum infecting dose;
Li the ratio of the number of dead (due to the specific cause) animals when infected with the given dose to the total number of animals to which this dose was administered; and
$\Sigma$ Li the sum of the Li values found for all tested doses.

The protection factor is the ratio of the value of LD50 of the immunized animals to the value of LD50 of the intact animals.

The data obtained indicate the presence of a significant nonspecific immunity-stimulating action in the preparation. The LD50 value of the culture of *S. typhimurium* (a heterologous pathogen) in the experimental group ($14.45 \cdot 10^6$ live microbes) was 6.75 times higher than that in the control group of animals ($2.14 \cdot 10^6$ live microbes).

It should also be noted that the lifespan was increased in the vaccinated animals when infected with the maximum dose (of the used ones) of the causative agent of *salmonellosis* in comparison with a similar group of intact animals: the average lifespan after infection was 6.5 and 3.5 days in vaccinated animals (group 5/1) and intact ones (group 5/2), respectively.

Thus, the studies conducted show that the claimed preparation has a nonspecific immunity-stimulating effect with a predominant influence on the T-cell immunity. The preparation in therapeutic use effectively affects tumors of various histogenesis.

The invention claimed is:

1. A method of treatment of solid tumors in a subject in need thereof, comprising the steps of:
   (a) preparing a mixture of native or inactivated corpuscular microbial antigens of the following *Treponema pallidum* culture strains: (i) strain IX, (ii) strains VII or VIII, and (iii) Reiter strain or strain V, wherein said mixture is provided in the form of a pharmaceutical suspension containing from 0.4 to 0.6 mg/ml of said microbial antigens in terms of dry matter; and
   (b) parenterally administering to the subject a therapeutically effective amount of the pharmaceutical suspension, thereby increasing a differentiation of NK-cells, T helper cells, cytotoxic T lymphocyte and expression of INF-γ in the subject.

2. The method according to claim 1, wherein said antigens are heat-inactivated and phenol-preserved.

3. The method according to claim 1, wherein the step (a) further includes the step of: adding to said mixture a phenolized sodium chloride physiological saline solution with a concentration of phenol 0.25±0.02%, thereby obtaining said pharmaceutical suspension additionally containing from 2.3 to 2.7 mg/ml of phenol.

4. The method according to claim 1, wherein said mixture is prepared for inactivated corpuscular microbial antigens only; the step (a) further includes the steps of:
   preparing inoculum of *Treponema pallidum* culture strains (i)-(iii) in meat-peptone broth with beef liver pieces under anaerobic conditions at a temperature of (37±1°) C during 7-10 days;
   cultivating said inoculum in an artificial thioglycolic in a shaker-incubator at 120±10 rpm during 7-10 days thereby obtaining a microbial suspension;
   providing a deposition of said microbial suspension for 22-24 hours;
   providing a partial decantation from 60 to 80% of a total volume of said microbial suspension thereby obtaining a concentrated microbial suspension;
   at a temperature of (58±2°) C, providing thermoinactivation of the concentrated microbial suspension for 60 min;
   providing a preservation of the concentrated microbial suspension by addition phenol to a final concentration of 0.5±0.1%; and
   providing purification of the concentrated microbial suspension by filtration and subsequent washing thereof with a physiological sodium chloride solution with adding phenol to a final concentration of 0.5±0.1% thereby obtaining said inactivated corpuscular microbial antigens.

5. The method according to claim 1, wherein said mixture is prepared for native corpuscular microbial antigens only, the step (a) further includes the steps of:
   preparing inoculum of *Treponema pallidum* culture strains (i)-(iii) in meat-peptone broth with beef liver pieces under anaerobic conditions at a temperature of (37±1°) C during 7-10 days;
   cultivating said inoculum in an artificial thioglycolic in a shaker-incubator at 120±10 rpm during 7-10 days thereby obtaining a microbial suspension;
   providing a deposition of said microbial suspension for 22-24 hours;
   providing a partial decantation from 60 to 80% of a total volume of said microbial suspension thereby obtaining a concentrated microbial suspension; and
   providing purification of the concentrated microbial suspension by washing thereof with a physiological sodium chloride solution thereby obtaining said native corpuscular microbial antigens.

6. A method for prevention of solid tumors in a subject in need thereof, comprising the steps of:
   (a) preparing a mixture of native or inactivated corpuscular microbial antigens of the following *Treponema pallidum* culture strains: (i) strain IX, (ii) strains VII or VIII, and (iii) Reiter strain or strain V, wherein said mixture is provided in the form of a pharmaceutical suspension containing from 27.0 to 29.0 mg/ml of said microbial antigens in terms of dry matter; and
   (b) parenterally administering to the subject a therapeutically effective amount of the pharmaceutical suspension, thereby increasing a differentiation of NK-cells, T helper cells, cytotoxic T lymphocyte and expression of INF-γ in the subject.

7. The method according to claim 6, wherein said antigens are heat-inactivated, adsorbed on aluminum hydroxide and phenol-preserved.

8. The method according to claim 6, wherein the step (a) further includes the step of: adding to said mixture a phenolized sodium chloride physiological saline solution with a concentration of phenol 0.25±0.02%, and aluminum hydroxide, thereby obtaining said pharmaceutical suspension additionally containing from 2.3 to 2.7 mg/ml of phenol and from 1.2 to 1.4 mg/ml of aluminum ions.

9. The method according to claim 6, wherein said mixture is prepared for inactivated corpuscular microbial antigens only; the step (a) further includes the steps of:
    preparing inoculum of *Treponema pallidum* culture strains (i)-(iii) in meat-peptone broth with beef liver pieces under anaerobic conditions at a temperature of (37±1°) C during 7-10 days;
    cultivating said inoculum in an artificial thioglycolic in a shaker-incubator at 120±0.10 rpm during 7-10 days thereby obtaining a microbial suspension;
    providing a deposition of said microbial suspension for 22-24 hours;
    providing a partial decantation from 60 to 80% of a total volume of said microbial suspension thereby obtaining a concentrated microbial suspension;
    at a temperature of (58±2°) C, providing thermoinactivation of the concentrated microbial suspension for 60 min;
    providing a preservation of the concentrated microbial suspension by the addition of phenol to a final concentration of 0.5±0.1%; and
    providing purification of the concentrated microbial suspension by filtration and subsequent washing thereof with a physiological sodium chloride solution with adding phenol to a final concentration of 0.5±0.1%, thereby obtaining said inactivated corpuscular microbial antigens.

10. The method according to claim 6, wherein said mixture is prepared for native corpuscular microbial antigens only; the step (a) further includes the steps of:
    preparing inoculum of *Treponema pallidum* culture strains (i)-(iii) in meat-peptone broth with beef liver pieces under anaerobic conditions at a temperature of (37±1°) C during 7-10 days;
    cultivating said inoculum in an artificial thioglycolic in a shaker-incubator at 120±0.10 rpm during 7-10 days thereby obtaining a microbial suspension;
    providing a deposition of said microbial suspension for 22-24 hours;
    providing a partial decantation from 60 to 80% of a total volume of said microbial suspension thereby obtaining a concentrated microbial suspension; and
    providing purification of the concentrated microbial suspension by washing thereof with a physiological sodium chloride solution thereby obtaining said native corpuscular microbial antigens.

* * * * *